US007608401B2

(12) United States Patent
Pietrangelo

(10) Patent No.: US 7,608,401 B2
(45) Date of Patent: Oct. 27, 2009

(54) MUTATIONS IN THE FERROPORTIN 1 GENE ASSOCIATED WITH HEREDITARY HAEMOCHROMATOSIS

(76) Inventor: Antonello Pietrangelo, Via San Martino Mugnano, 3/1, Modena (IT) I-41100

( * ) Notice: Subject to any disclaimer, the term of this patent is extended or adjusted under 35 U.S.C. 154(b) by 0 days.

(21) Appl. No.: 11/942,653

(22) Filed: Nov. 19, 2007

(65) Prior Publication Data
US 2008/0145855 A1    Jun. 19, 2008

Related U.S. Application Data

(62) Division of application No. 10/399,488, filed as application No. PCT/EP01/12018 on Oct. 17, 2001, now Pat. No. 7,317,097.

(30) Foreign Application Priority Data
Oct. 17, 2000    (IT)    ............ MI2000A2240

(51) Int. Cl.
*C07H 21/04*    (2006.01)
*C12Q 1/68*    (2006.01)

(52) U.S. Cl. .............. 435/6; 435/91.1; 435/91.2; 536/23.1; 536/24.3

(58) Field of Classification Search ............ None
See application file for complete search history.

(56) References Cited

OTHER PUBLICATIONS

Abboud et al. J. of Biol. Chemistry, vol. 275, No. 26, pp. 19906-19912, 2000.*
Genbank AF215636 , *Homo sapiens* SLC1A3 iron transporter mRNA, Jul. 2, 2000.*
International Search Report from PCT/EP01/12018, Nov. 15, 2002, Pietrangelo.
Abboud et al., "A Novel Mammalian Iron-Regulated Protein In Intracellular Iron Metabolism," (2000) JBC, 275:19906-19912.
Abravaya et al., "Detection of Point Mutations With A Modified Ligase Chain Reaction (Gap-LCR)," (1995) Nucleic Acids Research, 23:675-682.
Barany, "Genetic Disease and DNA Amplification Using Cloned Thermostable Ligase," (1991) PNAS, 88:189-193.
Borot et al., "Mutations in the MHC Class I-Like Candidate Gene for Hemochromatosis In French Patients," (1997) Immunogenetics, 45:320-324.
Chee et al., "Accessing Genetic Information With High-Density DNA Arrays," (1996) Science, 274:610-614.
Cotton et al., "Reactivity of Cytosine and Thymine In Single-Base-Pair Mismatches With Hyrdoxylamine and Osmium Tetroxide and Its Application to the Study of Mutations," (1988) PNAS, 85:4397-4401.
Cuff et al., "Evaluation and Improvement of Multiple Sequence Methods for Protein Secondary Structure Prediction," (1999) Proteins: Structure, Function, and Genetics, 34:508-519.
Faham et al., "A Novel In Vivo Method to Detect DNA Sequence Variaton," (1995) Genome Research, 5:474-482.

Fahy et al., "Self-Sustained Sequence Replication (3SR): An Isothermal Transcription-Based Amplification System Alternative to PCR," (1991) PCR Methods and Applications, 1:25-33.
Feder et al., "A Novel MHC Class I-Like Gene Is Mutated In Patients With Hereditary Haemochromatosis," (1996) Nature Genetics, 13:399-408.
Fleming et al., "Ferroportin Mutation In Autosomal Dominant Hemochromatosis: Loss Of Function, Gain In Understanding," (2001) The Journal of Clinical Investigation, 108:521-522.
Guldberg et al., "'Broad-Range' DGGE For Single-Step Mutation Scanning of Entire Genes: Application to Human Phenylalanine Hydroxylase Gene," (1994) Nucleic Acids Research, 22:880-881.
Kan et al., "Antenatal Diagnosis of Sickle-Cell Anemia By DNA Analysis of Amniotic Fluid Cells," (1978) The Lancet, 910-911.
Landegren et al., "A Ligase-Mediated Gene Detection Technique," (1988) Science, 241:1077-1080.
Maskos et al., "A Novel Method For The Parallel Analysis of Multiple Mutations In Multiple Samples," (1993) Nucleic Acids Research, 21:2269-2270.
Meyers et al., "Detection of Single Base Substitutions By Ribonuclease Cleavage at Mismatches in RNA:DNA Duplexes," (1985) Science, 230:1242-1246.
Montosi et al., "Autosomal-Dominant Hemochromatosis Is Associated With A Mutation In The Ferroprotein (SLC11A3) Gene," (2001) The Journal of Clinical Investigation, 108:619-623.
Newton et al., "Analysis Of Any Point Mutation In DNA. The Amplification Refractory Mutation System (ARMS)," (1989) Nucleic Acids Research, 17:2503-2516.
Nikiforov et al., "Genetic Bit Analysis: A Solid Phase Method For Typing Single Nucleotide Polymorphisms," (1994) Nucleic Acids Research, 22:4167-4175.
Pietrangelo et al., "Hereditary Hemochromatosis In Adults Without Pathogenic Mutations In The Hemochromatosis Gene," (1999) NEJM, 341:725-732.
Piperno et al., "Heterogeneity of Hemochromatosis In Italy," (1998) Gastroenterology, 114:996-1002.
Ravnik et al., "Sensitivity of Single-Strand Conformation Polymorphism and Heteroduplex Method For Mutation Detection In The Cystic Fibrosis Gene," (1994) Human Molecular Genetics, 3:801-807.
Rost et al., "Prediction of Protein Secondary Structure at Better than 70% Accuracy," (1993) J. Mol. Biol., 232:584-599.
Saiki et al., "Genetic Analysis of Amplified DNA With Immobilized Sequence Specific Oligonucleotide Probes," (1989) PNAS, 86:6230-6234.

(Continued)

*Primary Examiner*—Jeanine A Goldberg
(74) *Attorney, Agent, or Firm*—Jones Day

(57) ABSTRACT

The present invention relates to mutations in the gene coding for ferroportin 1 associated with hereditary haemochromatosis and methods for the diagnosis of hereditary haemochromatosis based on the identification of such mutations.

13 Claims, 2 Drawing Sheets

OTHER PUBLICATIONS

Saiki et al., "Primer-Directed Enzymatic Amplification of DNA With A Thermostable DNA Polymerase," (1988) Science, 239:487-491.

Sambrok et al., "Molecular Cloning Laboratory Manual," $2^{nd}$ Edition, 189, pp. 17.2, 17.25, 17.34, 17.36.

Syvanen et al., "From Gels to Chips: "Minisequencing" Primer Extension For Analysis of Point Mutations and Single Nucleotide Polymorphisms," (1999) Human Mutation, 13:1-10.

Syvanen et al., "A Primer Guided Nucleotide Incorporation Assay In The Genotyping of Apolipoprotein E," (1990) Genomics, 8:684-692.

Wallace et al., "Hybridization of Synthetic Oligodeoxyribonucleotides to $\Phi_x$ 174 DNA: The Effect of Single Base Pair Mismatch," (1979) Nucleic Acids Research, 6:3543-3557.

Walker et al., "Isothermal In Vitro Amplification of DNA By A Restriction Enzyme /DNA Polymerase System," (1992) PNAS, 89:392-396.

Winter et al., "A Method To Detect and Characterize Point Mutations in Transcribed Genes: Amplification and Overexpression of the Mutant c-Ki-ras Allele in Human Tumor Cells," (1985) PNAS, 82:7575-7579.

Wu et al., "The Ligation Amplification Reaction (LAR)-Amplification of Specific DNA Sequences Using Sequential Rounds of Template-Dependent Ligation," (1989) Genomics, 4:560-569.

Youil et al., "Screening For Mutations By Enzyme Mismatch Cleavage With T4 Endonuclease," (1995) PNAS, 92:87-91.

Genbank Accession No. AF215636 "*Homo sapiens* SLC11A3 Iron Transporter mRNA, Complete CDS," Last Accessed On May 7, 2003.

Genbank Accession No. AI634604, Last Accessed On May 7, 2003.

* cited by examiner

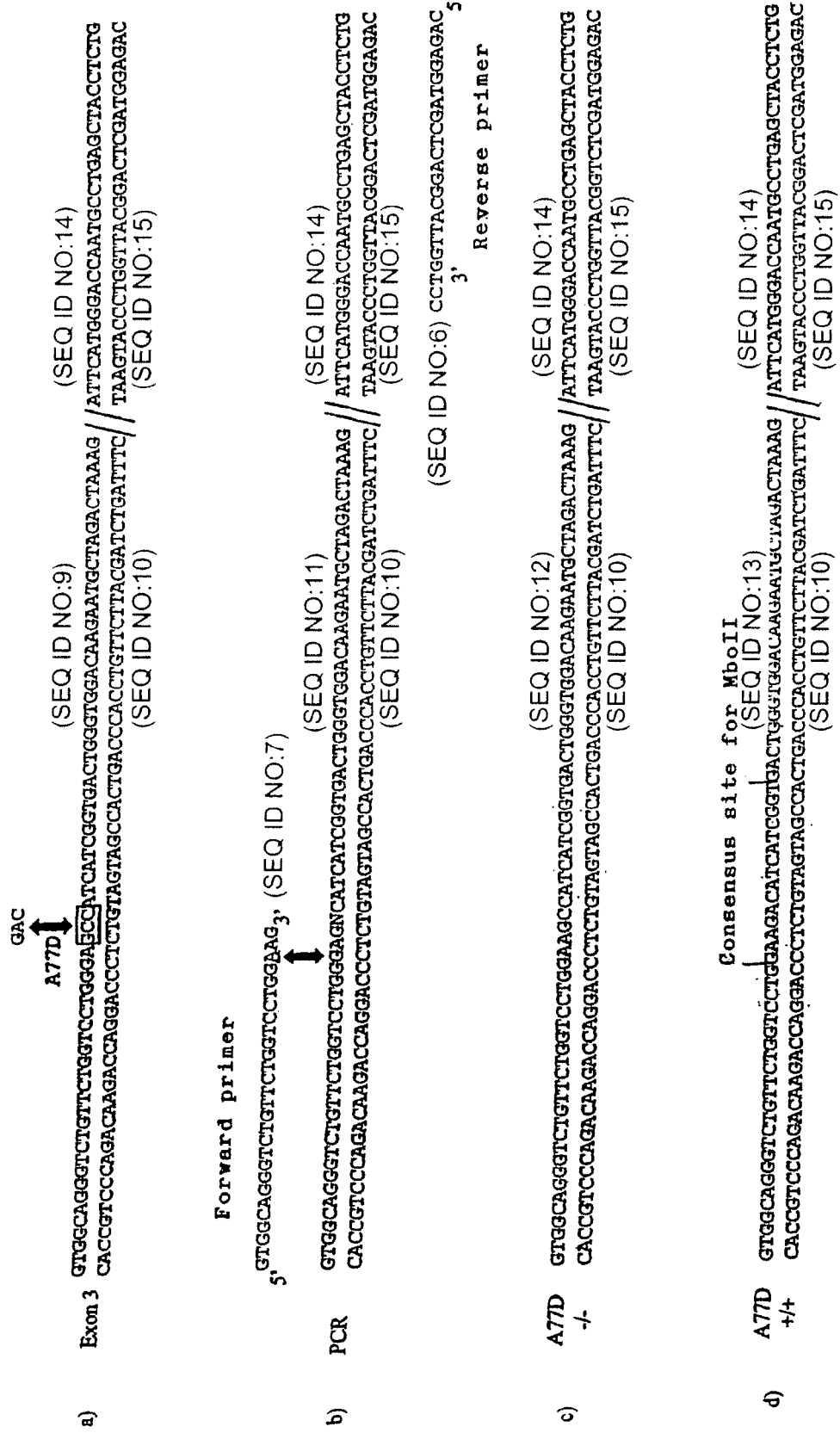

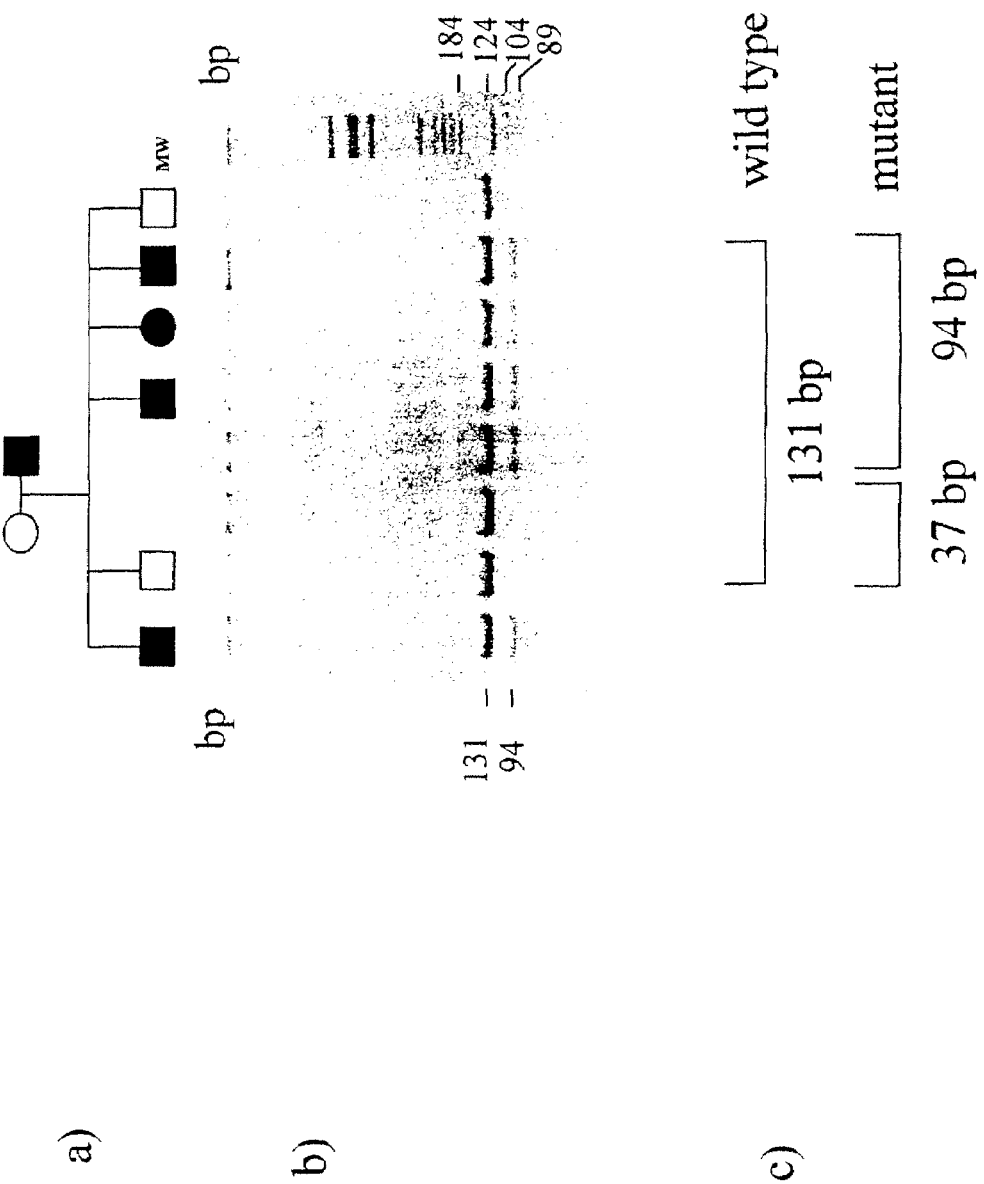

MUTATIONS IN THE FERROPORTIN 1 GENE ASSOCIATED WITH HEREDITARY HAEMOCHROMATOSIS

CROSS REFERENCE TO RELATED APPLICATIONS

This application is a divisional application of U.S. application Ser. No. 10/399,488, filed Aug. 27, 2003, which is a U.S. national stage application of PCT Application No. PCT/EP01/12018, filed Oct. 17, 2001, which claims priority to Italian Application No. MI2000A002240, filed Oct. 17, 2000, each of which is incorporated herein by reference in its entirety for all purposes.

FIELD OF THE INVENTION

The present invention concerns mutations in the gene coding for ferroportin 1 associated with hereditary haemochromatosis and the identification of such mutations as a diagnostic method for hereditary haemochromatosis.

STATE OF THE ART

Haemochromatosis is a hereditary pathology characterised by an excessive accumulation of iron in the organism, which over time leads to lesions of different organs and tissues, particularly liver, myocardium, pancreas, kidney, spleen, gonads and skin. Idiopathic haemochromatosis is the most widespread hereditary disease in the Western population (incidence 1:300) and is characterised by a recessive transmission. Recently this type of haemochromatosis has been associated with mutations of the HFE gene, located on the short arm of chromosome 6. In a study carried out on patients suffering from this pathology in fact, it was observed that 83% of the analyzed subjects had a single point mutation at this gene (C282Y) (Feder et al, Nat Genet 1996, 13: 399-408).

However, more recent studies have shown that in the Mediterranean population only 64% of patients suffering from hereditary haemochromatosis are homozygotes for the C282Y mutation. This suggests that, in the southern European population in particular, other genes besides HFE may be responsible for idiopathic haemochromatosis (Piperno et al, Gastroenterology 1998, 114: 996-1002 and Borot et al, Immunogentics 1997, 45: 320-324).

The identification of the genetic modifications responsible for hereditary haemochromatosis is of great diagnostic and therapeutic importance. Up to now, the diagnosis of haemochromatosis occurs too late and is based on the clinical symptomatology that develops as a result of often irreversible tissue injury. Besides, diagnosis of this pathology is made difficult by the fact that its symptoms are often similar to those of other pathologies characterised by altered iron homeostasis.

The development of genetic screening methods for the early diagnosis, at presymptomatic stage, of hereditary haemochromatosis would allow a timely phlebotomy intervention before damage to organs and tissues occurs. Furthermore, the identification of genetic alterations associated with hereditary haemochromatosis and the understanding of the role that they play in the development of the pathology are of extreme importance for the setting up of new and improved therapeutic strategies.

SUMMARY OF THE INVENTION

The inventor has previously identified and characterised a family suffering from a form of non HFE-dependent haemochromatosis with a autosomal dominant inhertance pattern, (Pietrangelo et al, New Eng J Med 1999, 341: 725-732).

The inventor has now surprisingly found that the locus of this pathology is on the long arm of chromosome 2 (2q32) and that subjects suffering from this type of haemochromatosis have a mutation at a codon located in the hexone 3 of the gene coding for ferroportin 1, that is situated in the same chromosomal region, which is not observed in subjects who are not suffering from the pathology. This mutation leads to the substitution of an amino acid in the ferroportin 1 molecule.

Therefore the present invention refers to a nucleic acid coding for a mutated ferroportin 1 characterised by a mutation of the codon coding for the amino acid corresponding to position 77 of SEQ. ID. No. 2, a mutated ferroportin 1 protein coded by said nucleic acid and methods for the in vitro diagnosis of hereditary haemochromatosis based on the identification of said nucleic acid or said protein.

DESCRIPTION OF THE FIGURES

FIG. 1: Outline of the strategy for the identification of the mutation by means of enzymatic digestion with MboII, described in Example 3.

In detail:

FIG. 1a shows the genomic DNA sequence in the diagnostic method, in which the framed GCC sequence is the codon coding for the amino acid alanine in position 77 of the wild type ferroportin that is mutated to the GAC codon in individuals suffering from hereditary haemochromatosis. The double bar (II) denotes the separation between hexone 3 and a segment of the intron 3.

FIG. 1b shows the primers used in the PCR reaction of the diagnostic method described in Example 3b and the target genomic DNA sequence in which N stands for the C or A nucleotide. The forward primer has a mismatched nucleotide, which is underlined (A instead of G).

FIG. 1c shows the amplified sequence from control individuals, in the absence of the mutation.

FIG. 1d shows instead the amplified DNA sequence from individuals suffering from the pathology in which, in one of the alleles, the GCC codon is mutated to the GAC codon and leads to the appearance of a consensus site for the Mbo II enzyme.

FIG. 2: Results of the diagnostic analysis on healthy family members or on family members suffering from haemochromatosis.

In detail:

FIG. 2a shows the relationship between the analyzed individuals (pedigree). The subjects suffering from haemochromatosis are represented in black, while the healthy ones are in white. The circles represent the female subjects and the squares males.

FIG. 2b shows the restriction profiles, following digestion with Mbo II, of the DNA amplified from each individual.

As shown in FIG. 2c, in the case of healthy subjects, having only the wild type sequence, following digestion with Mbo II, the 131 base pair amplified DNA is not digested. Since all the subjects suffering from the pathology are heterozygotes for the mutation, the amplified DNA from these patients is digested in a band of 131 base pairs (normal allele) and two bands of 94 and 37 base pairs (the latter is not visible in FIG. 2b).

DETAILED DESCRIPTION OF THE INVENTION

As will be shown in detail in the examples which follow, the authors of the present invention have identified that the mutation of a particular codon located in the hexone 3 of the ferroportin 1 gene is associated with a form of hereditary haemochromatosis that is not dependent on the HFE gene.

The identified mutation leads to the expression of a mutated ferroportin 1 in which the amino acid alanine, in a position corresponding to position 77 of SEQ ID No: 2 (sequence listing enclosed), is replaced.

The inventor has surprisingly found that the above mutation is a sufficient indication of the presence of hereditary haemochromatosis not linked to the HFE gene, and that therefore its identification is useful for the early diagnosis of this pathology. Besides, the authors of the present invention have found that hereditary haemochromatosis is correlated with the functional impairment of ferroportin 1. Therefore, according to a first aspect the present invention relates to a nucleic acid coding for a mutated ferroportin 1 characterised in that it comprises a mutation of the codon coding for the amino acid corresponding to position 77 of SEQ ID NO: 2. The term "nucleic acid coding for a ferroportin 1" means a genomic DNA, cDNA, DNA, for example obtained through PCR, or mRNA coding for the amino acid sequence of SEQ ID NO: 2 or for an amino acid sequence having at least 90% and preferably at least 95% homology with said amino acid sequence. When the nucleic acid is DNA this may be a single or double helix.

In addition, the invention comprises a nucleic acid with a sequence which is complementary to that of the aforesaid nucleic acid. For instance, this sequence can be an antisense sequence used to stop, the expression of the gene or of the mRNA in the cells.

The mutation, according to the invention, leads to the substitution, in the molecule of wild-type ferroportin 1 (GenBank accession number: AF231121) of the amino acid corresponding to position 77.

The term "wild-type ferroportin 1" refers to a ferroportin 1 which carries out its normal and physiological role, in particular that is without mutations which alter its functionality. Besides, the numerical position of the amino acid has the sole purpose of identifying it and may vary due to the presence of variations in the amino acid sequence of the protein, for instance with changes in the species taken into consideration or because of the presence of mutations or deletions in the regions upstream Of said amino acid.

The inventor has found that the substitution of the alanine in position 77 with a molecule of aspartic acid results in a structural modification in ferroportin 1 which may be shown, for example, by prediction programs of protein secondary structure, namely "PHDsec" (Rost et al, J. Mol Biol 232: 584-599, 1993) and "JRED" (Cuff et al, Proteins: Structure, Function Genetics and 34: 508-519). In particular, said substitution determines the passage of the protein region that goes from amino acid 58 to amino acid 81 (LLLTAVYGL-WAGS VLVLGXIIGD, SEQ ID NO: 8) from the alpha-helix to beta-layer configuration.

The importance of the amino acid in position 77 in determining the secondary structure of ferroportin 1 is also confirmed by its high conservation among different animal species.

The substitution of alanine, a small and uncharged amino acid, with a charged and larger molecule such as aspartic acid, results in steric and electrostatic interactions that destabilize the alpha helix hydrogen bonds. Similarly, substitutions of alanine with charged amino acids such as, for instance, arginine, lysine or glutamic acid or with amino acids of greater sterical hinderance, for instance histidine, can lead to a similar distorsion of the molecule.

Furthermore, the ferroportin 1 region corresponding to SEQ ID NO 8 contains a post-transductional modification site of the protein, the myristilation site GAIIGD, that is altered in the mutated protein according to the invention. As is known, myristilation is important in helping the interactions of polypeptides with membrane phospholipids.

Therefore, according to a second aspect, the invention relates to a mutated ferroportin 1 protein characterised by the substitution of the amino acid in a position corresponding to position 77 of SEQ ID NO: 2 and coded by the nucleic acid as above.

Said substitution consists in the substitution of the amino acid alanine in a position corresponding to position 77, with an amino acid having different steric and/or electrostatic properties from those of alanine. Preferably, said amino acid is selected from the group including arginine, lysine, glutamic acid or aspartic acid, among which aspartic acid is preferred.

Therefore, according to a particularly preferred application, the mutation present in the nucleic acid of the invention consists in the substitution of the codon coding for the amino acid in a position corresponding to position 77 of SEQ ID NO: 2, preferably GCC, with a codon chosen from the group including GAC and GAU, among which GAC is preferred.

In a further aspect of the invention relates to peptides with an amino acid sequence of at least 6 amino acids comprising the amino acid corresponding to position 77 of SEQ ID NO: 2 and the amino acids immediately downstream and/or upstream of this. The length and sequence of such peptides are selected on the basis of criteria known to a person skilled in the art according to the desired application, for instance, to stimulate the production in host animals of antibodies specific for the mutation or to obtain peptides and/or antibodies that specifically interact with the mutated epitope.

A preferred embodiment of such peptides is the peptide corresponding to SEQ ID NO: 8, in which Xaa is preferably aspartic acid.

The present invention also relates to nucleotide fragments of the aforesaid nucleic acid comprising the mutated codon, and oligonucleotides with a sequence of at least 9 nucleotides and preferably at least 15 nucleotides of the aforesaid nucleic acid including said codon.

Said fragments and oligonucleotides can be of RNA or DNA and, in the latter case, single or double helix. Preferably, the oligonucleotides of the invention are single helix.

Furthermore the invention includes nucleotide fragments and oligonucleotides with sequences complementary to those of the aforesaid fragments or oligonucleotides. By "nucleotide fragment", according to the present invention, is meant a nucleic acid with a sequence corresponding to a partial sequence of the nucleic acid of the invention having a length exceeding 100 base pairs.

By "oligonucleotide" according to the present invention, is meant a fragment of the nucleic acid of the invention of a maximum length of 100 base pairs.

The nucleotide fragments and oligonucleotides of the invention may be obtained, for instance, by digestion of the nucleic acid of the invention, through amplification by PCR or synthesized using techniques known in the art.

The oligonucleotides and the DNA fragments of the invention are used for different purposes such as, for instance, the production of chimeric proteins or antibodies, the determination of the mutation of the invention for diagnostic purposes or the inactivation of the mutated gene for therapeutic purposes. A person skilled in the art is able to choose fragments and oligonucleotides of having sequence and length suitable for the desired uses. For instance, should said fragments or oligonucleotides be used for the determination of the mutation of invention with hybridization techniques, they must be of a length and sequence so as to be capable of hybridizing in a specific way, under stringent conditions, at a nucleic acid sequence comprising the mutated codon.

According to a preferred embodiment, the fragments and oligonucleotides of the invention are labelled, for instance, with radioisotopes, enzymes, biotin-avidin or other molecules which allow them to be visualized through specific assays.

Moreover, the invention relates to the peptides coded by such fragments and oligonucleotides.

The nucleic acid, of the invention, a fragment thereof comprising the mutation or a nucleic acid comprising such fragment can be advantageously used for the production of a recombinant mutated ferroportin 1, a fragment of it or a chimeric protein including this fragment, in order to, for instance, study the functional characteristics of the mutated protein, for example through competition studies, or produce antibodies. To this purpose, said nucleic acid or fragment is inserted into an expression vector which, in turn, is introduced into a procaryotic or eucaryotic cell using techniques well known in the art such as transfection, transformation, infection or intranuclear injection.

Vectors suitable for this purpose include plasmids, vectors of viral origin and yeast or mammalian artificial chromosomes.

Accordingly, in a further aspect, the invention relates to a recombinant vector comprising a nucleic acid or a DNA fragment according to the invention as well as to eucaryotic or procaryotic cells comprising said vector.

The nucleic acid according to the invention can be used for the preparation of eucaryotic cells, tissues or non-human animals comprising a transgene coding for the mutated ferroportin 1 of the invention. The transgene can be permanently inserted into the genome of the cell, tissue or animal or be present in extrachromosomial form.

Said cells, tissues or non-human animals are useful as models to study the function of the gene and of the protein comprising the mutation of the invention, as well as their role in the onset of hereditary haemochromatosis. This study is of particular importance for the development of new therapeutic approaches for the treatment of hereditary haemochromatosis.

In a further aspect, the invention refers to a method for the in vitro diagnosis of hereditary haemochromatosis in a mammal, preferably Homo Sapiens, comprising the following steps:

a) isolation of genomic DNA or RNA from a biological sample obtained from said mammal;

b) testing for the presence, in said genomic DNA or RNA, of the mutation according to the invention, Wherein the presence of said mutation is an indication that said mammal is suffering from hereditary haemochromatosis.

Preferably said biological sample is a sample of plasma, saliva, urine, faeces, amniotic fluid or tissue.

Prior to testing, the RNA is preferably transformed into complementary DNA (cDNA) through a reverse transcription reaction.

The genomic DNA or the cDNA are analyzed directly or following in vitro amplification polymerase chain reaction (PCR) (Saiki et al, Science 239: 487-491, 1988) or other techniques, for instance, ligase chain reaction (LCR) (Wu et al, genomics 4: 560-569, 1989) strand displacement amplification (SDA) (Walker et al, PNAS USA 89: 392-396) or self-sustained sequence replication (3SR) (Fahy et al, PCR methods Appl. 1: 25-33, 1992).

Preferably, the genomic DNA or the cDNA is amplified through PCR using a pair of oligonucleotides (primers) suitable for the amplification of a segment of said DNA comprising the codon coding for the amino acid corresponding to position 77 of SEQ ID NO: 2.

For instance, pairs of primers that can be used to amplify the cDNA are those with the nucleotide sequence of SEQ ID No: 3 and SEQ ID No: 4 whereas primers suitable for the amplification of the genomic DNA are those with the nucleotide sequence of SEQ ID No: 5 and SEQ ID No: 6.

Numerous techniques, well known in the art, can be used to determine the presence of the mutation according to the invention in the genomic DNA or the cDNA. Suitable techniques are, for instance, techniques based on the use of restriction enzymes (Kan et al, Lancet: 910-912, 1978), hybridization techniques with allele-specific oligonucleotide probes (Wallace et al, Nucl Acids Res 6: 3543-3557, 1978) among which, for instance, hybridization with oligonucleotides immobilized on filters (Saiki et al, PNAS USA 86: 6230-6234, 1989) or micro-chips (Chee et al, Science 274: 610-614, 1996) and oligonucleotide arrays (Maskos et al, Nucl Acids Res 21: 2269-2270, 1993), allele-specific PCR (Newton et al Nucl Acid Res 17: 2503-2516, 1989), mismatch repair detection (MRD) (Faham and Cox Genome Res: 474-482, 1995), Single-strand conformational polymorphism analysis (Ravnik-Glavac et al, Hum. Mol. Gen. 3: 801, 1994), gel electrophoresis in denaturant gradient (Guldberg et al., Nucl. Acids Res. 22: 880, 1994), Hot Cleavage (Cotton et al Proc. Natl. Acad Ski USA 85: 4397, 1988), DNAse (Youil et al, PNAS USA 92: 87-91, 1995) and RNAse protection assay (Winter et al. Proc. Natl. Acad. Ski. USA, 82: 7575, 1985; Meyers et al, Science 230: 1242, 1985), allele specific primer extension (Syvanen et al, genomics 8: 684-692, 1990 and Syvanen et al, Hum Mutat 13: 1-10, 1999), genetic bit analysis (GBA) (Nikiforov et al Nucl Acid Res 22: 4167-4175, 1994), primer-ligation assay (OLA) (Landergen et al, Science 241: 1077, 1988), allele specific ligation chain reaction (LCR) (Barrany PNAS USA 88: 189-193, 1991), gap-LCR (Abravaya et al Nucl Acids Res 23: 675-682, 1995) and sequencing techniques. Particularly preferred techniques for the determination of the mutation of the invention are techniques based on the use of restriction enzymes, allele specific PCR, hybridization and sequencing techniques. Therefore, according to a first preferred application, the testing for the presence of the mutation according to the invention in the analyzed DNA occurs using techniques based on the use of restriction enzymes and comprises the following steps:

a) amplification of the genomic DNA or cDNA with a pair of oligonucleotides suitable for the selective amplification of a segment of said DNA including the codon coding for the amino acid corresponding to position 77 of SEQ ID NO: 2 and the concurrent introduction into the amplified DNA of such a mutation which, in the presence of the mutation of the invention, creates the consensus sequence for a restriction site otherwise not present;

b) incubation of the amplified DNA with an enzyme which is able to recognize said restriction site; and c) analysis of the size of the digestion products;

wherein the occurring of digestion is a sign of the presence of the mutation of the invention in the genomic or complementary DNA.

The analysis of the size of the digestion products may be carried out, for instance, through gel electrophoresis, using a marker of molecular weights, followed by visualization of the DNA bands using, for example, ethidium bromide.

In order to test, for example, for the presence of the substitution of the GCC codon, coding for alanine in position 77, with the GAC codon, coding for an aspartic acid molecule, oligonucleotides can be used with the nucleotide sequence of SEQ ID NO: 6 and SEQ ID NO: 7. As will be shown in the examples that follow, these oligonucleotides give rise, in the presence of the aforesaid substitution, to a fragment of amplified DNA with the sequence shown in FIG. 1d which contains the consensus site for the Mbo II enzyme, GAAGACAT-CATCGGT, not present in the fragment of DNA amplified from the wild-type DNA (FIG. 1c). The subsequent incubation of the product of the amplification reaction with Mbo II results in the fragment being digested only if the mutation was present in the original sequence. According to a further preferred application, the determination of the mutation according to the invention is performed through hybridization techniques in which fragments of the nucleic acid of the invention or oligonucleotides specific for the mutation according to the invention are used.

Said fragments or oligonucleotides are capable of hybridizing, in a specific way, at a sequence of the nucleic acid of the invention comprising the mutated codon also when said sequence is present together with many other sequences.

A person skilled in the art is able to select each time the hybridization conditions and the length and sequence of the fragments or the oligonucleotides most suitable for the particular hybridization technique used and the kind of DNA that is being analyzed (genomic or complementary DNA, amplified or cloned in appropriate vectors).

According to a further preferred application, the diagnostic method envisages the use of allele-specific PCR, in which the genomic or complementary DNA undergoes a PCR reaction in which oligonucleotides are used which are able to selectively amplify a segment of said DNA including the mutated codon and not the corresponding segment including the wild-type codon.

In addition the present invention also relates to nucleic acid fragments and oligonucleotides according to the invention to be used in the aforesaid methods. In particular, it refers to oligonucleotides with the nucleotide sequence corresponding to SEQ ID NO: 3, 4, 5, 6 and 7.

Within the scope of the present invention are also included diagnostic kits for the identification, in an individual, of the mutation according to the invention. According to a particularly preferred application, said diagnostic kits comprise oligonucleotides with a nucleotide sequence corresponding to SEQ ID NO: 6 and 7 and the Mbo II enzyme.

The present invention also relates to a method for the in vitro diagnosis of hereditary haemochromatosis in mammals including testing for the presence, in a biological sample from said mammal, of a mutated ferroportin 1 protein according to the invention, wherein the identification of said protein is an indication that the individual is suffering from hereditary haemochromatosis.

Preferably said testing is performed through immunological assays in which monoclonal or polyclonal antibodies are used which are able to discriminate between a molecule of mutated ferroportin, according to the invention, and a molecule of wild-type ferroportin.

Therefore the present invention also refers to monoclonal or polyclonal antibodies which are able to specifically recognize a molecule of mutated ferroportin 1 according to the invention, or on epitope thereof comprising the mutation. Such antibodies are obtained using methods well known in the art such as those described by Harlow and Lane in Antibodies, A Laboratory Manual, Cold Spring Harbour Laboratory 1988.

The antibodies of the invention are particularly useful, as well as diagnostic reagents, in studying the characteristics of the protein or for therapeutic purposes. For instance, said antibodies can be used to determine the exact tissular or cellular localization of the mutated protein, to study its biochemical characteristics or to purify it by immunoaffinity.

Moreover, since the presence in an individual of a gene bearing the mutation of the invention and of the ferroportin 1 coded by it is correlated with the onset of hereditary haemochromatosis it is very important to have means to stop expression of the gene or to inactivate the protein.

Therefore, the invention also relates to oligonucleotides, for instance antisense oligonucleotides, suitable for inhibiting the expression of the gene coding for mutated ferroportin 1 of the invention, and antibodies and polypeptides able to specifically alter the functionality of the mutated ferroportin 1 of the invention.

In addition, the invention relates to pharmaceutical compositions comprising said oligonucleotides, antibodies or peptides mixed with pharmaceutically acceptable excipients.

EXAMPLES

Example 1

Identification of the Chromosome and the Chromosomal Locus Associated with Non HFE-Dependent Hereditary Haemochromatosis A DNA sample was extracted from the peripheral blood of the proband and family members suffering from the pathology using Quiagen Blood Extraction Kit (Quiagen).

The DNA extracted was then used for a genome wide-search that was performed by using the ABI PRISM Linkage mapping set (Perkin Elmer, United States). Fluorescent oligonucleotides were used for the PCR reactions, under the conditions suggested by the manufacturer. An aliquot of each PCR reaction was then sequenced in an ABI PRISM 377 DNA sequencer and the results obtained were analyzed using GENESCAN software. The assignment of the allele was carried out using Genotyper™ software. Statistical analysis was performed based on a dominant autosomal disease with complete penetrance. The gene-disease frequency was fixed at 0.012 and all the marker alleles were considered to be equally frequent. Table 1 contains the lod score, i.e. the maximum probability of association of a specific marker with the disease.

TABLE 1

| | Z at θmax | | | | | | | | |
|---|---|---|---|---|---|---|---|---|---|
| Marker | .00 | .01 | .05 | .1 | .2 | .3 | .4 | Zmax | (θmax) |
| D2S2257 | .20 | .20 | .19 | .16 | .11 | .06 | .02 | .20 | (.000) |
| D2S364 | $-\infty$ | 3.46 | 3.82 | 3.67 | 3.00 | 2.08 | .99 | 3.82 | (.040) |

TABLE 1-continued

| Marker | Z at θmax | | | | | | | Zmax | (θmax) |
|---|---|---|---|---|---|---|---|---|---|
| | .00 | .01 | .05 | .1 | .2 | .3 | .4 | | |
| D2S350 | −∞ | 2.82 | 3.16 | 2.99 | 2.31 | 1.44 | .53 | 3.16 | (.040) |
| D2S152 | 5.88 | 5.78 | 5.38 | 4.85 | 3.74 | 2.51 | 1.16 | 5.88 | (.000) |
| D2S118 | 5.99 | 5.89 | 5.49 | 4.96 | 3.84 | 2.60 | 1.23 | 5.99 | (.000) |
| D2S280 | −∞ | 2.35 | 2.77 | 2.70 | 2.22 | 1.53 | .70 | 2.78 | (.060) |
| D2S315 | 3.46 | 3.41 | 3.17 | 2.87 | 2.22 | 1.48 | .66 | 3.46 | (.000) |
| D2S117 | −∞ | 2.69 | 3.09 | 3.00 | 2.47 | 1.71 | .76 | 3.09 | (.050) |

The higher the score, expressed logarithmically, the lower the probability that the association of the disease with the specific markers used is casual. For example, a lod score of 1.0 denotes 1 chance in 10 that the result is due to chance; a lod score of 2, one chance in 100 and so on. The fact that the markers D2S118 (5.99) and D2S152 (5.88) gave very high scores shows that the gene associated with the disease is situated in the region delimited by these markers. Ferroportin 1 is situated in this chromosomal region. No other chromosomal region gave similar results.

Example 2

Identification of the Mutation

Blood samples were taken from the proband, from 15 family members suffering from the pathology and from 25 family members not suffering from the pathology. Total RNA was isolated from macrophages obtained from each sample by extraction in guanidine-isothiocyanate and the complementary DNA was then prepared according to a standard protocol (400 ng of total RNA, 1 µg of oligodT, 1 mM of dNT, 20 U of reverse trascripted AMV in 20 µl of reaction buffer; Promega) The complete ferroportin 1 sequence was then amplified from the cDNA through a PCR reaction using the following oligonucleotide pairs:

```
Forward primer
5'-GCTCAGGGCGTCCGCTAGGCT-3'    (SEQ.ID.NO 3)

reverse primer:
5'-GGCTTACACCCTCATGTTCT-3'     (SEQ ID NO: 4)
```

In detail, 10 ml of the product of the reverse transcription reaction were amplified in 50 µl (final volume) of 1× reaction buffer containing 200 µM dNTP, 1.5 mM MgCl2, 0.25 µg of each of the above described oligonucleotide, 2.6 units of enzyme. A 30 cycle program was used for the amplification reaction, each of which was characterised by the following heat profile:

94° C. for 1 minute,
58° C. for 40 seconds,
75° C. for 5 minutes.

From the amplified ferroportin 1 cDNA, four partially overlying DNA fragments were then obtained through a new PCR, using the following oligonucleotide pairs:

```
1° fragment:
Forward primer: 5'-GCTCAGGGCGTCCGCTAGGCT-3'
Reverse primer: 5'-CAGACACCGCAAAGTGCCACA-3'

2° fragment:
Forward primer: 5'-ACCTCGCTGGTGGTACAG-3'
Reverse primer: 5'-CCGCAAGCAAAGAGCTTG-3'

3° fragment:
Forward primer: 5'-GGTGCTATCTCCAGTTCCTT-3'
Reverse primer: 5'-AGACGTACTCCACGCACA-3'

4° fragment:
Forward primer: 5'-TCAGTCTCCTTTGTGGCA-3'
Reverse primer: 5'-GGCTTACACCCTCATGTTCT-3'
```

The four fragments obtained from the amplification were then electrophoretically separated on agarose gel, purified using the Jet Sorb kit (Genenco) and sequenced directly using the Rhodamine Sequence kit (Perkin Elmer, United States). Sequencing revealed the presence, in subjects suffering from the pathology, of the substitution of a C with an A in position 230 of SEQ. ID No. 1 (nucleotide in position 534 of the sequence having GenBank accession number: AF231121), that was not found in any of the control subjects. This substitution is located in hexone 3 of the ferroportin 1 gene and results in the substitution of alanine with aspartic acid at position 77 of ferroportin 1.

Example 3

Diagnostic Method a) genomic DNA of the proband, of 15 family members suffering from the pathology and 125 control individuals, including 100 healthy volunteers and 25 family members not suffering from the pathology, was extracted from leukocytes obtained from blood samples of the subjects to be analyzed using a blood DNA extraction kit (Quiagen).

The DNA obtained was then amplified by PCR using a pair of oligonucleotides complementary to the intronic regions flanking hexone 3 and having the following sequence:

```
Forward primer:
5'-CCTTTTGATAAGGAAGCAACTTCC-3'   (SEQ ID NO: 5)

Reverse primer:
5'-CAGAGGTAGCTCAGGCATTGGTCC-3'   (SEQ ID NO: 6)
```

In detail, 200 ng of genomic DNA were amplified in 50 µl of 1× reaction buffer containing 200 µM dNTPs, 1.5 mM MgCl2, 20 pmoles of each oligonucleotide and 2.6 U of enzyme.

A 30 cycle program was used for the amplification reaction, each of which was characterised by the following heat profile:

94° C. for 1 minute,
60° C. for 1 minute,
72° C. for 45 seconds.

The DNA obtained was then purified using the PCR Wizard kit (Promega) and sequenced in an automatic ABI Prism 377 sequencer (Perkin Elmer, United States), with the same pair of oligonucleotides used for the PCR reaction.

The substitution of a C with an A in hexone 3 was found in the subjects suffering from the pathology, but not in the control subjects.

b) blood samples were obtained from the proband, from 15 family members suffering from the pathology and from the 125 control subjects described in example 2 and the genomic DNA was extracted using the blood DNA extraction kit (Biorad).

Since the mutation observed does not give rise to the appearance or disappearance of any restriction site, the portion of hexone 3 containing the mutation was amplified by PCR using a pair of oligonucleotides with the following sequences:

```
Forward primer:
5'-GTGGCAGGGTCTGTTCTGGTCCTGGAAG-3'     (SEQ.ID NO.7)

Reverse primer:
5'-CAGAGGTAGCTCAGGCATTGGTCC-3'         (SEQ.ID NO.6)
```

As shown in FIG. 1b, the forward primer has a mismatched nucleotide (A instead of G, underlined). Amplification with the aforesaid oligonucleotides gives rise, in the presence of the mutation, to an amplified DNA fragment, having the sequence shown in FIG. 1d, that contains the consensus site for the Mbo II enzyme, GAAGACATCATCGGT. On the contrary, in the absence of the mutation, a DNA fragment with the sequence shown in FIG. 1d is obtained and which does not contain such a restriction site (FIG. 1c).

Therefore, the subsequent incubation of the product of the amplification reaction with the Mbo II enzyme results in the digestion of the fragment only if the original sequence contained the mutation.

In detail, 10 µl of the extracted genomic DNA were amplified in a final 50 µl of 1× reaction buffer containing 200 µM dNTPs, 1.5 mM MgCl2, 20 pmoles of each oligonucleotide and 2.6 units of enzyme. A 30 cycle program was used for the amplification reaction, each cycle being characterised by the following heat profile:

94° C. for 1 minute,
58° C. for 1 minute,
72° C. for 45 seconds.

10 µl of the product obtained from the amplification were then digested with the Mbo II enzyme (Geneco) in 1× reaction buffer for 3 hours at 37° C.

The fragments obtained from the digestion were then separated on a 12% polyacrylamide gel. The samples obtained from patients suffering from the pathology resulted in 3 bands of 131, 94 and 37 base pairs. On the contrary, all the control samples gave had just one band of 131 base pairs. FIG. 2 shows the results obtained from the proband, from 4 family members suffering from the pathology and from 3 healthy family members. As can be seen from the figure, digestion of the fragment of 131 base pairs into two fragments of 94 and 37 base pairs was only observed in subjects suffering from the pathology.

Also comprised in the present invention is any therapeutic operation involving the substitution of the mutated gene with the wild type gene. Therefore, the mutated ferroportin 1 molecule is a therapeutic target for all genic therapy operations aimed at the substitution of the mutated gene.

The invention claimed is:

1. A method of determining a predisposition to hereditary haemochromatosis in a human, the method comprising:
   a) isolating a nucleic acid encoding a ferroportin 1 protein from the human, wherein the ferroportin 1 protein comprises SEQ ID NO:2; and
   b) detecting if a codon sequence in the nucleic acid encodes aspartic acid at position 77 of SEQ ID NO:2 to determine if the human is predisposed to suffer from hereditary haemochromatosis;
   wherein it is determined that the human is predisposed to suffer from hereditary haemochromatosis when the codon sequence in the nucleic acid is detected to encode aspartic acid at position 77 of SEQ ID NO:2.

2. The method of claim 1, wherein step (a) comprises obtaining a biological sample from the human, wherein the biological sample comprises the nucleic acid encoding ferroportin 1 protein and the biological sample is a sample of blood, plasma, saliva, urine, faeces, amniotic fluid or tissue.

3. The method of claim 1, wherein the isolated nucleic acid is genomic DNA.

4. The method of claim 3, wherein step (b) comprises amplifying the nucleic acid by PCR using a pair of oligonucleotides suitable for the amplification of a segment of the nucleic acid comprising the codon encoding the amino acid at position 77 of SEQ ID NO: 2.

5. The method of claim 4, wherein said pair of oligonucleotides has the nucleotide sequences of SEQ.ID NO: 5 and SEQ.ID NO: 6.

6. The method of claim 1, wherein the isolated nucleic acid is RNA.

7. The method of claim 6, wherein step (b) comprises reverse transcribing the RNA to produce cDNA.

8. The method of claim 7, further comprising amplifying the cDNA by PCR using a pair of oligonucleotides suitable for the amplification of a segment of said cDNA comprising the codon encoding the amino acid at position 77 of SEQ ID NO: 2.

9. The method of claim 8 wherein said pair of oligonucleotides has the nucleotide sequences of SEQ.ID NO: 3 and SEQ.ID NO: 4.

10. The method of claim 1 wherein said detecting in step (b) comprises using a technique selected from techniques based on the use of restriction enzymes, hybridization techniques with allele-specific oligonucleotide probes, allele-specific PCR, mismatch repair detection, single-strand conformational polymorphism analysis, gel electrophoresis in denaturant gradient, Hot Cleavage, DNAse and RNAse protection assay, allele specific primer extension, genetic bit analysis oligonucleotide-ligation assay, allele specific ligation chain reaction and sequencing techniques.

11. The method of claim 10 wherein said technique used is selected from techniques based on the use of restriction enzymes, allele specific PCR, hybridization or sequencing techniques.

12. The method of claim 1 wherein said detecting in step (b) comprises:
   amplifying the isolated nucleic acid with oligonucleotides suitable for the selective amplification of a segment of said nucleic acid including the codon encoding the amino acid at position 77 of SEQ ID NO: 2 to produce an amplification product, wherein the amplification product comprises a consensus sequence for a restriction site when the codon encoding the amino acid at position 77 of SEQ ID NO:2 encodes an aspartic acid, and wherein the consensus sequence is absent when the codon encoding the amino acid at position 77 of SEQ ID NO:2 encodes an alanine;
   incubating the amplification product with a restriction enzyme which is able to recognize said restriction site; and
   analyzing of the size of the restriction enzyme digestion products.

13. The method of claim 12, wherein said pair of oligonucleotides has the nucleotide sequences of SEQ ID NO: 6 and SEQ ID NO: 7, and wherein said enzyme is Mbo II.

* * * * *

SEQUENCE LISTING

```
<160> NUMBER OF SEQ ID NOS: 8

<210> SEQ ID NO 1
<211> LENGTH: 1716
<212> TYPE: DNA
<213> ORGANISM: Homo sapiens
<220> FEATURE:
<221> NAME/KEY: CDS
<222> LOCATION: (1)..(1716)
<220> FEATURE:
<221> NAME/KEY: misc_feature
<222> LOCATION: (229)..(231)
<223> OTHER INFORMATION: nnn is gcc, gac, or gau

<400> SEQUENCE: 1 atg acc agg gcg gga gat cac aac cgc cag aga gga tgc tgt gga tcc        48
Met Thr Arg Ala Gly Asp His Asn Arg Gln Arg Gly Cys Cys Gly Ser
1               5                   10                  15 ttg gcc gac tac ctg acc tct gca aaa ttc ctt ctc tac ctt ggt cat        96
Leu Ala Asp Tyr Leu Thr Ser Ala Lys Phe Leu Leu Tyr Leu Gly His
                20                  25                  30 tct ctc tct act tgg gga gat cgg atg tgg cac ttt gcg gtg tct gtg       144
Ser Leu Ser Thr Trp Gly Asp Arg Met Trp His Phe Ala Val Ser Val
            35                  40                  45 ttt ctg gta gag ctc tat gga aac agc ctc ttt tgg aca gca gtc tac       192
Phe Leu Val Glu Leu Tyr Gly Asn Ser Leu Leu Thr Ala Val Tyr
    50                  55                  60 ggg ctg gtg gtg gca ggg tct gtt ctg gtc ctg gga nnn atc atc ggt       240
Gly Leu Val Val Ala Gly Ser Val Leu Val Leu Gly Xaa Ile Ile Gly
65                  70                  75                  80
```

```
gac tgg gtg gac aag aat gct aga ctt aaa gtg gcc cag acc tcg ctg       288
Asp Trp Val Asp Lys Asn Ala Arg Leu Lys Val Ala Gln Thr Ser Leu
             85                  90                  95 gtg gta cag aat gtt tca gtc atc ctg tgt gga atc atc ctg atg atg       336
Val Val Gln Asn Val Ser Val Ile Leu Cys Gly Ile Ile Leu Met Met
            100                 105                 110 gtt ttc tta cat aaa cat gag ctt ctg acc atg tac cat gga tgg gtt       384
Val Phe Leu His Lys His Glu Leu Leu Thr Met Tyr His Gly Trp Val
        115                 120                 125 ctc act tcc tgc tat atc ctg atc atc act att gca aat att gca aat       432
Leu Thr Ser Cys Tyr Ile Leu Ile Ile Thr Ile Ala Asn Ile Ala Asn
    130                 135                 140 ttg gcc agt act gct act gca atc aca atc caa agg gat tgg att gtt       480
Leu Ala Ser Thr Ala Thr Ala Ile Thr Ile Gln Arg Asp Trp Ile Val
145                 150                 155                 160 gtt gtt gca gga gaa gac aga agc aaa cta gca aat atg aat gcc aca       528
Val Val Ala Gly Glu Asp Arg Ser Lys Leu Ala Asn Met Asn Ala Thr
                165                 170                 175 ata cga agg att gac cag tta acc aac atc tta gcc ccc atg gct gtt       576
Ile Arg Arg Ile Asp Gln Leu Thr Asn Ile Leu Ala Pro Met Ala Val
            180                 185                 190 ggc cag att atg aca ttt ggc tcc cca gtc atc ggc tgt ggc ttt att       624
Gly Gln Ile Met Thr Phe Gly Ser Pro Val Ile Gly Cys Gly Phe Ile
        195                 200                 205 tcg gga tgg aac ttg gta tcc atg tgc gtg gag tac gtc ctc ctc tgg       672
Ser Gly Trp Asn Leu Val Ser Met Cys Val Glu Tyr Val Leu Leu Trp
    210                 215                 220 aag gtt tac cag aaa acc cca gct cta gct gtg aaa gct ggt ctt aaa       720
Lys Val Tyr Gln Lys Thr Pro Ala Leu Ala Val Lys Ala Gly Leu Lys
225                 230                 235                 240 gaa gag gaa act gaa ttg aaa cag ctg aat tta cac aaa gat act gag       768
Glu Glu Glu Thr Glu Leu Lys Gln Leu Asn Leu His Lys Asp Thr Glu
                245                 250                 255 cca aaa ccc ctg gag gga act cat cta atg ggt gtg aaa gac tct aac       816
Pro Lys Pro Leu Glu Gly Thr His Leu Met Gly Val Lys Asp Ser Asn
            260                 265                 270 atc cat gag ctt gaa cat gag caa gag cct act tgt gcc tcc cag atg       864
Ile His Glu Leu Glu His Glu Gln Glu Pro Thr Cys Ala Ser Gln Met
        275                 280                 285 gct gag ccc ttc cgt acc ttc cga gat gga tgg gtc tcc tac tac aac       912
Ala Glu Pro Phe Arg Thr Phe Arg Asp Gly Trp Val Ser Tyr Tyr Asn
    290                 295                 300 cag cct gtg ttt ctg gct ggc atg ggt ctt gct ttc ctt tat atg act       960
Gln Pro Val Phe Leu Ala Gly Met Gly Leu Ala Phe Leu Tyr Met Thr
305                 310                 315                 320 gtc ctg ggc ttt gac tgc atc acc aca ggg tac gcc tac act cag gga      1008
Val Leu Gly Phe Asp Cys Ile Thr Thr Gly Tyr Ala Tyr Thr Gln Gly
                325                 330                 335 ctg agt ggt tcc atc ctc agt att ttg atg gga gca tca gct ata act      1056
Leu Ser Gly Ser Ile Leu Ser Ile Leu Met Gly Ala Ser Ala Ile Thr
            340                 345                 350 gga ata atg gga act gta gct ttt act tgg cta cgt cga aaa tgt ggt      1104
Gly Ile Met Gly Thr Val Ala Phe Thr Trp Leu Arg Arg Lys Cys Gly
        355                 360                 365 ttg gtt cgg aca ggt ctg atc tca gga ttg gca cag ctt tcc tgt ttg      1152
Leu Val Arg Thr Gly Leu Ile Ser Gly Leu Ala Gln Leu Ser Cys Leu
    370                 375                 380 atc ttg tgt gtg atc tct gta ttc atg cct gga agc ccc ctg gac ttg      1200
Ile Leu Cys Val Ile Ser Val Phe Met Pro Gly Ser Pro Leu Asp Leu
```

-continued

```
                385                 390                 395                 400
tcc gtt tct cct ttt gaa gat atc cga tca agg ttc att caa gga gag   1248
Ser Val Ser Pro Phe Glu Asp Ile Arg Ser Arg Phe Ile Gln Gly Glu
                405                 410                 415 tca att aca cct acc aag ata cct gaa att aca act gaa ata tac atg   1296
Ser Ile Thr Pro Thr Lys Ile Pro Glu Ile Thr Thr Glu Ile Tyr Met
            420                 425                 430 tct aat ggg tct aat tct gct aat att gtc ccg gag aca agt cct gaa   1344
Ser Asn Gly Ser Asn Ser Ala Asn Ile Val Pro Glu Thr Ser Pro Glu
        435                 440                 445 tct gtg ccc ata atc tct gtc agt ctg ctg ttt gca ggc gtc att gct   1392
Ser Val Pro Ile Ile Ser Val Ser Leu Leu Phe Ala Gly Val Ile Ala
    450                 455                 460 gct aga atc ggt ctt tgg tcc ttt gat tta act gtg aca cag ttg ctg   1440
Ala Arg Ile Gly Leu Trp Ser Phe Asp Leu Thr Val Thr Gln Leu Leu
465                 470                 475                 480 caa gaa aat gta att gaa tct gaa aga ggc att ata aat ggt gta cag   1488
Gln Glu Asn Val Ile Glu Ser Glu Arg Gly Ile Ile Asn Gly Val Gln
                485                 490                 495 aac tcc atg aac tat ctt ctt gat ctt ctg cat ttc atc atg gtc atc   1536
Asn Ser Met Asn Tyr Leu Leu Asp Leu Leu His Phe Ile Met Val Ile
            500                 505                 510 ctg gct cca aat cct gaa gct ttt ggc ttg ctc gta ttg att tca gtc   1584
Leu Ala Pro Asn Pro Glu Ala Phe Gly Leu Leu Val Leu Ile Ser Val
        515                 520                 525 tcc ttt gtg gca atg ggc cac att atg tat ttc cga ttt gcc caa aat   1632
Ser Phe Val Ala Met Gly His Ile Met Tyr Phe Arg Phe Ala Gln Asn
    530                 535                 540 act ctg gga aac aag ctc ttt gct tgc ggt cct gat gca aaa gaa gtt   1680
Thr Leu Gly Asn Lys Leu Phe Ala Cys Gly Pro Asp Ala Lys Glu Val
545                 550                 555                 560 agg aag gaa aat caa gca aat aca tct gtt gtt tga                   1716
Arg Lys Glu Asn Gln Ala Asn Thr Ser Val Val
                565                 570
```

<210> SEQ ID NO 2
<211> LENGTH: 571
<212> TYPE: PRT
<213> ORGANISM: Homo sapiens
<220> FEATURE:
<221> NAME/KEY: misc_feature
<222> LOCATION: (77)..(77)
<223> OTHER INFORMATION: The 'Xaa' at location 77 is either Asp or Ala
      depending on the variability of position 229-231 from SEQ ID
      NO. 1.

<400> SEQUENCE: 2

```
Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Xaa Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
```

-continued

```
                100                 105                 110
Val Phe Leu His Lys His Glu Leu Leu Thr Met Tyr His Gly Trp Val
            115                 120                 125

Leu Thr Ser Cys Tyr Ile Leu Ile Ile Thr Ile Ala Asn Ile Ala Asn
130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
            340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
            420                 425                 430

Ser Asn Gly Ser Asn Ser Ala Asn Ile Val Pro Glu Thr Ser Pro Glu
        435                 440                 445

Ser Val Pro Ile Ile Ser Val Ser Leu Leu Phe Ala Gly Val Ile Ala
    450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
            500                 505                 510

Leu Ala Pro Asn Pro Glu Ala Phe Gly Leu Leu Val Leu Ile Ser Val
        515                 520                 525
```

```
Ser Phe Val Ala Met Gly His Ile Met Tyr Phe Arg Phe Ala Gln Asn
    530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570
```

<210> SEQ ID NO 3
<211> LENGTH: 21
<212> TYPE: DNA
<213> ORGANISM: Artificial sequence
<220> FEATURE:
<223> OTHER INFORMATION: Description of artificial sequence: PCR primer

<400> SEQUENCE: 3
gctcagggcg tccgctaggc t                                               21

<210> SEQ ID NO 4
<211> LENGTH: 20
<212> TYPE: DNA
<213> ORGANISM: Artificial sequence
<220> FEATURE:
<223> OTHER INFORMATION: Description of artificial sequence: PCR primer

<400> SEQUENCE: 4
ggcttacacc ctcatgttct                                                 20

<210> SEQ ID NO 5
<211> LENGTH: 24
<212> TYPE: DNA
<213> ORGANISM: Artificial sequence
<220> FEATURE:
<223> OTHER INFORMATION: Description of artificial sequence: PCR primer

<400> SEQUENCE: 5 cctttttgata aggaagcaac ttcc                                           24

<210> SEQ ID NO 6
<211> LENGTH: 24
<212> TYPE: DNA
<213> ORGANISM: Artificial sequence
<220> FEATURE:
<223> OTHER INFORMATION: Description of artificial sequence: PCR primer

<400> SEQUENCE: 6
cagaggtagc tcaggcattg gtcc                                            24

<210> SEQ ID NO 7
<211> LENGTH: 28
<212> TYPE: DNA
<213> ORGANISM: Artificial sequence
<220> FEATURE:
<223> OTHER INFORMATION: Description of artificial sequence: PCR primer

<400> SEQUENCE: 7
gtggcagggt ctgttctggt cctggaag                                        28

<210> SEQ ID NO 8
<211> LENGTH: 24
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: Xaa is Asp or Ala

```
<400> SEQUENCE: 8

Leu Leu Leu Thr Ala Val Tyr Gly Leu Val Val Ala Gly Ser Val Leu
1               5                   10                  15

Val Leu Gly Xaa Ile Ile Gly Asp
            20
```